(12) United States Patent
Leban et al.

(10) Patent No.: US 7,317,030 B2
(45) Date of Patent: Jan. 8, 2008

(54) COMPOUNDS AS INHIBITORS OF CELL PROLIFERATION AND VIRAL INFECTIONS

(75) Inventors: Johann Leban, Germering (DE); Harald Schmitt, Mainz (DE)

(73) Assignee: 4SC AG, Martinsried (DE)

( * ) Notice: Subject to any disclaimer, the term of this patent is extended or adjusted under 35 U.S.C. 154(b) by 74 days.

(21) Appl. No.: 11/066,265

(22) Filed: Feb. 28, 2005

(65) Prior Publication Data

US 2005/0197368 A1  Sep. 8, 2005

Related U.S. Application Data

(60) Provisional application No. 60/547,432, filed on Feb. 26, 2004.

(51) Int. Cl.
*A61K 31/421* (2006.01)
*C07D 263/34* (2006.01)

(52) U.S. Cl. .................... 514/377; 548/233
(58) Field of Classification Search ............ 514/236.8, 514/377; 544/139; 548/233
See application file for complete search history.

(56) References Cited

U.S. PATENT DOCUMENTS 4,191,767 A  3/1980 Warner, Jr. et al.

FOREIGN PATENT DOCUMENTS

| DE | 2 345 972 | 3/1974 |
|---|---|---|
| EP | 0 709 225 B1 | 8/1998 |
| WO | WO 96/40673 | 12/1996 |
| WO | WO 97/40028 | 10/1997 |
| WO | WO 9740028 A1 * | 10/1997 |
| WO | WO 02/070467 A1 | 9/2002 |

OTHER PUBLICATIONS

Ambinter Screening Library Catalog, CAS Registry No. 502878-32-2, cited on Applicant's IDS as XP-002290758.*
Ambinter Screening Library Catalog, CAS Registry No. 380462-73-7, cited on Applicant's IDS as XP-002290758.*
Chemical Abstracts, "Ambinter Screening Library", XP-002290758, Jan. 1, 2004.
Chemical Abstracts, "Ambinter Screening Library", XP-002290755, Jan. 1, 2004.
Chemical Abstracts, "Enamine Screening Library", XP-002290759, Jun. 30, 2004.
Chemical Abstracts, "Enamine Screening Library", XP-002290756, Jun. 30, 2004.
Database Chemabs 'Online!, N-(1'-Ethyl-2'pyrrolidinylmethyl)-2-methoxy-5-sulfamoylbenzoic acid amide, AN 93: 186157, JP 55-055160, XP-002290760, Apr. 22, 1980.
Database Chemabs 'Online!, "5-(3-Halo- or ethylaminopropyl)-2-o-methoxyphenyl-4,5-dihydrooxazoles", AN 88:105310, JP 52-106865, XP-002290761, Sep. 7, 1977.
"Handbook of Fine Chemicals and Laboratory Equipment", XP-002290757, 2003, 1 page.
Joseph Daniel, et al., Reactions of Chlorosulfonyl Isocyanate with Thiazolines and Oxazolines: Formation of Thiazolo and Oxazolothiadizines.; Synthetic Communications, vol. 23, No. 1, XP-008033490, 1993, pp. 121-129.

* cited by examiner

*Primary Examiner*—Rebecca Anderson
*Assistant Examiner*—Michael P. Barker
(74) *Attorney, Agent, or Firm*—Womble Carlyle Sandridge & Rice; Mark D. Jenkins, Esq.

(57) ABSTRACT

The present invention relates to novel compounds of the general formula (I) and salts and physiologically functional derivatives thereof, $$\left[\begin{array}{c} R^1 \\ A \\ R^2 \end{array}\right]\!\!-\!\!Z\!\!-\!\!\left[Y\!\!-\!\!NH\right]_m\!\!-\!\!\left[\!\!\begin{array}{c} \phantom{x} \\ \phantom{x} \\ R^4 \end{array}\!\!\right]_n\!\!-\!\![O_2S\!-\!NR^5R^6]_p$$

wherein
Z is NH, or $CH_2$ if Y is $SO_2$
Y is C=O, C=S, or $SO_2$ if Z is $CH_2$;
A is phenyl or indolyl, N-methyl-indolyl
$R^1$ is —CN, wherein the bond between $CR^3$ and $CR^7$ is a single or double bond;
m is 0 or 1;
n is 0 or 1;
p is 0 or 1;
and to their use as medicaments.

8 Claims, No Drawings

COMPOUNDS AS INHIBITORS OF CELL PROLIFERATION AND VIRAL INFECTIONS

The present invention relates to compounds which are suitable for the therapy of diseases that can be treated by modulating cellular pathways in eukaryotes as for instance cancer, immunological or inflammatory disorders and viral infections. Further processes for the preparation of these compounds, and to their use.

T cell homeostasis is critical for the maintenance of immune tolerance. Defects in T-cell homeostasis can lead autoimmune pathology. Autoimmune disease includes a large spectrum of clinically distinct entities that share a common aetiology, a misguided, self-directed immune response.

This immune response can also be the consequence of an organ transplant.

Evidence suggests a prime role of T cell reactivity in Autoimmune diseases. Measuring proliferative responses in T lymphocytes is a widely used assay to measure immune competence (Killestein J et al. *J Neuroimmunol*, 133, 217-24, 2002).

We used a nonradioactive technique for the measurement of in vitro T-cell proliferation (Messele T et al. *Clinical and Diagnostic Laboratory Immunology*, 687-692, 2002).

Peripheral blood mononuclear cells (PBMCs) were isolated from human blood obtained from volunteer donators. PBMCs were isolated by centrifugation in ACCUSPIN tubes using HISTOPAQUE.

PBMCs were stimulated with PHA and cell proliferation was measured with a Roche calorimetric BromUridin incorporation ELISA kit.

Regulation of the immune response is controlled by a variety of signalling pathways such as T-cell or TNF receptor signalling (Chen G et al. *Science*, 296 1634-1640, 2002). To further characterize targets of compounds which we found active in the T-cell proliferation assay, we tested the compounds on a variety of targets involved in such pathways. Compounds described here are inhibitors of T-lymphocyte proliferation were active on three molecular targets: Kv1.3 ion channels and Inosine Monophosphate Dehydrogenase (IMPDH) and the human proteasome. The compounds described may act on one of these targets specifically or on several targets simultaneously.

Kv1.3 ion channel

Activated T lymphoblasts respond more effective to mitogenic stimuli than resting T-cells, partly through differences in $Ca^{2+}$ signalling which in turn is dependent on $K^+$ channel activity. Kv1.3 channels and IK ion channels are up-regulated in T-lymphoblasts (Chang M C et al. *Cell Physiol Biochem*, 11(3), 123-34, 2001; Schlichter L C et al. *Recept Channels*, 1, 201-215, 1993). The gene encoding Kv1.3 channels was cloned and functional channels were expressed in cell lines (Grissmer S et al. *Mol Pharm*, 248, 478, 1995).

Selective blockers of Kv1.3 channels were found to be peptides from scorpion venom. One such toxin, noxiustoxin, blocks Kv1.3 currents with an $IC_{50}$ of 0.2 nM and inhibits T-lymphocyte proliferation with an $IC_{50}$ of 8 nM (Kath J C et al. *Ann Rev in Med Chem*, 32, 181-190, 1997).

A role for Kv1.3 in lymphocyte activation was suggested by the observation a selective Kv 1.3 channel blocker inhibits proliferation and interleukin-2 production in stimulated T-lymphocytes (Beeton et al. *J Immunol*, 166, 936-944, 2001).

The peptide toxin, Charybdotoxin, was shown to inhibit Kv1.3 ion channels and specifically bind to T-lymphocytes (Deutsch C, et al. *J Biol Chem*, 3668-3674, 1991). Charybdotoxin also inhibits IK channels in T-lymphocytes. Both IK and Kv1.3 are involved in T-lymphocyte proliferation. Blockage of Kv1.3 has been better studied as an immunsuppressant (Kath J C, *Annu Rep Med Chem*, 181-190, 1997).

The inhibition of Kv1.3 was measured in stable transfected cell lines expressing mouse Kv1.3 using the patch-clamp technique (Rauer H et al. *J Biol Chem Vol*. 275, No. 2, 1201-1208, 2000), Rauer H *Mol Pharmacol*, 50, 1625-1634, 1996, Rauer H et al. *J Pharmacol*, 127, 1065-1074, 1999).

Small molecule Kv1.3 blockers have been described (Kath J C et al. *Bioorg Med Chem Lett*, 7, 8, 1047-1052, 1997; Nguyen A et al. *Mol Pharmacol*, 50, 6, 1672-1679, 1996; Shouwu M et al. Bioorg Med Chem Lett, 13, 6, 1161-1164, 2003).

Nevertheless none of these compounds has been reported to have entered clinical trials, probably due to specificity and thus toxicity problems. Therefore new Kv1.3 compounds with a favourable profile are needed. Here we report new compounds with such a potential.

IMPDH

The synthesis of nucleotides in organisms is required for the cells in those organisms to divide and replicate. Nucleotide synthesis in mammals may be achieved through one of two pathways: the de novo synthesis pathway or the salvage pathway. Different cell types use these pathways to a different extent.

Inosine-5'-monophosphate dehydrogenase (IMPDH, EC 1.1.1.205) is an enzyme involved in the de novo synthesis of guanosine nucleotides. IMPDH catalyses the NADH-dependent oxidation of inosine-5'-monophosphate (IMP) to xanthosine-5'-monophosphate (XMP) (Jackson R C et al. *Nature* 256, 331-333, 1975).

The reaction mechanism involves first, the binding of IMP to the enzyme. Then the cofactor NAD binds and the reduced cofactor, NADH, is released. Finally, the product, XMP, is also released. (Carr S F et al. *J Biol Chem* 268, 27286-27290, 1993).

Of the two isoforms of human IMPDH, type I and type II, type two is specifically expressed in proliferating T-Lymphocytes. The homology of the two isoforms in humans is 84% (Collart F R et al. *J Biol Chem*, 263, 15769-15772, 1988).

The de novo synthesis of guanosine nucleotides, is important for the proliferation T-lymphocytes. T-lymphocytes depend on the de novo pathway as opposed to the salvage pathway to be able to respond to a antigen or mitogen with a proliferative response Allison A C et al. *Lancet* II, 1179, 1975). Therefore IMPDH inhibitors are an attractive target to inhibit T-cell proliferation without inhibiting growth of other cells. This makes IMPDH inhibitors attractive agents to treat autoimmune diseases and graft versus host relations.

IMPDH is also known to play a role in the proliferation of human leukaemia (Nagai M et al. *Cancer Res*, 51, 3886-3890).

IMPDH has been also implicated in viral replication (Carr S F *J Biol Chem* 268, 27286-27290, 1983). As in the case with tumor cells and T-lymphocytes viral replication in cells depend on de novo nucleoside synthesis.

Several classes of IMPDH inhibitors are known (Sintchak M D et al. *Immunopharmacology* 47, 2000, 163-184).

A member of the substrate inhibitors, ribavirin is marketed as an co-therapy with α-Interferon or pegylated α-Interferon to treat Hepatitis C (Pegasys-Copegus, Ribavirin- Rebetol). The therapeutic potential of ribavirin is limited due to limited bio availability, broad cellular toxicity and lack of sustained response in mono therapy.

Mycophenolic acid is an uncompetitive inhibitor of human IMPDH and blocks the proliferative response of T-cells towards antigen (Allison A C et al. *Ann NY Acad Sci* 696, 63, 1993).

Mycophenolate mofetil (Cell Cept), a prodrug of mycophenolic acid is approved to prevent acute renal allograft rejection following kidney transplantation (Sollinger H W et al. *Transplantation* 60, 225-232, 1995).

Due to glucuronidation in vivo and enterohepatic recycling it is accumulated in the GI tract and causes undesirable side effects (Allison A C et al. *Immunological Rev* 136, 5-28, 1993) There remains a need for potent specific (Type II) IMPDH inhibitors to treat autoimmune diseases, viral infections and cancer.

Recently a series of potent non competitive IMPDH inhibitors have been published based on 3-Methoxy-5-oxazolyl-biphenylurea moiety EP 1366766, EP 1178797, EP 1127883, EP 1276739, EP 1196414, EP 1127054, EP 1126843, WO 03/101199, WO 03/099206, WO 03/035066, WO 03/059269, WO 03/055447.

We describe some compounds with similar features but the distinct difference that the compounds have a sulphonamide group in the second aromatic ring, no such compounds have been described yet.

It is an object of the present invention to provide alternative effective agents which can be used for the treatment of diseases which require the inhibition of IMPDH.

Accordingly, a novel class of compounds with an inhibitory effect on IMPDH, in particular human IMPDH, was found.

Proteasome:

The major neutral proteolytic activity in the cytosol and nucleus is the proteasome, a 20S (700 kDa) particle with multiple peptidase activities. The continual turnover of cellular proteins by the ubiquitin-proteasome pathway is used by the immune system to screen for the presence of abnormal intracellular proteins (Goldberg A L et al. *Nat Biotechnol* 15, 5, 538-43, 2000; Goldberg A L et al. *Nature* 357, 375, 1993).

The ubiquitin-proteasome pathway plays an essential role in the regulation of NF-κB activity, being responsible for the degradation of the inhibitor IκB-α. In order to be targeted for degradation by the proteasome, Iκα must first undergo selective phosphorylation at serine residues 32 and 36, followed by ubiquitinylation (Chen et al. *Cell* 84, 853, 1996; Brown et al. *Science* 267, 1485, 1995).

NFκ-B, a transcriptin factor, regulates the transcription of an important set of genes, involved in inflammatory responses (Baeuerle P A et al. *Cell* 87, 1, 13-20, 1996). Proteasome inhibitors block IκB-α degradation and NF-κ (Traeckner, et al. *EMBO J*, 13, 5433, 1994).

Patents decribing Proteasome inhibitors have been described in reviews (Adams J et al. *Ann Rev in Med Chem* 31, 279-288, 1996) and in patents U.S. Pat. No. 06,117,887, U.S. Pat. No. 5,834,487, WO 00/004954, WO 00/04954, WO 00/170204, WO 00/33654, WO 00/64863, WO 00/114324, WO 99/15183, WO 99/37666.

One such compound, named Valcade (Bortezomib), has been approved to treat multiple myeloma (Paramore A et al. *Nature Reviews*, 2, 611, 2003).

Here we describe novel chemical entities with proteasome inhibitory activity.

The present invention is therefore directed to compounds of the general formula (I) or a salt thereof, where

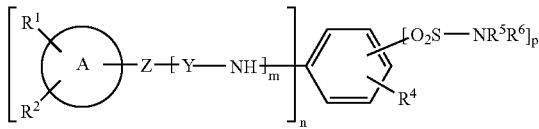

Z is NH, or CH if Y is $SO_2$
Y is C=O, C=S, or $SO_2$ if Z is CH;
A is phenyl or indolyl, N-methyl-indolyl
$R^1$ is —CN,

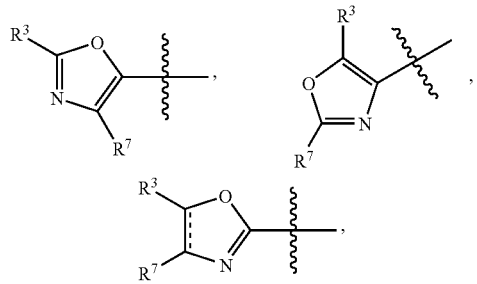

wherein the bond between $CR^3$ and $CR^7$ is a single or double bond;

$R^3$ is independently H, alkyl, cycloalkyl, aminoalkyl, alkoxy, —OH, —SH, alkylthio, hydroxyalkyl, haloalkyl, haloalkyloxy, aryl or heteroaryl;

$R^7$ is independently H, alkyl, cycloalkyl, aminoalkyl, alkoxy, —OH, —SH, alkylthio, hydroxyalkyl, haloalkyl, haloalkyloxy, aryl, arylalkyl or heteroaryl;

$R^2$ is a hydrogen, or an alkoxy, alkylthio, haloalkyloxy, group;

$R^4$ is independently H, alkyl, cycloalkyl, aminoalkyl, alkoxy, —OH, —SH, alkylthio, hydroxyalkyl, haloalkyl, haloalkyloxy, aryl, heteroaryl or

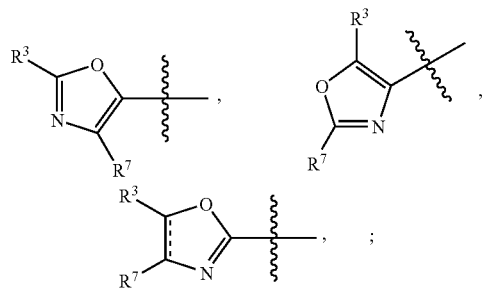

$R_5$ is independently H, alkyl, cycloalkyl, aminoalkyl, alkoxy, —OH, —SH, alkylthio, hydroxyalkyl, haloalkyl, haloalkyloxy, aryl, arylalkyl, haloaryl, haloalkylaryl, heteroaryl or $R^5$ and $R^6$ form a ring together with the N-atom to which they are attached [form a ring], the ring may or may not contain other hetero atoms including the O-atom or the atoms in the halogen group. When the ring formed by $R^5$ and $R^6$ with the N-atom contains additional O-atom, the ring may, for example, be a 6-membered morpholinyl ring;

$R^6$ is independently H, alkyl, cycloalkyl, aminoalkyl, alkoxy, —OH, —SH, alkylthio, hydroxyalkyl, haloalkyl, haloalkyloxy, aryl, arylalkyl, haloaryl, haloalkylaryl, heteroaryl or $R^6$ [is absent in the case it forms a ring together with $R^5$] and $R^5$ form a ring together with the N-atom to which they are attached, the ring may or may not contain other hetero atoms including the O-atom or the atoms in the halogen group. When the ring formed by $R^5$ and $R^6$ with the N-atom contains additional O-atom, the ring may, for example, be a 6-membered morpholinyl ring;

m is 0 or 1;

n is 0 or 1;

p is 0 or 1;

an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents R', preferably by halogen;

the $C_1$-$C_6$-alkyl, $C_1$-$C_6$-alkenyl and $C_1$-$C_6$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$—CH ($CH_3$)$_2$, —CH($CH_3$)—$C_2H_5$, —C($CH_3$)$_3$, —$C_5H_{11}$, —$C_6H_{13}$, —C(R")$_3$, —$C_2$(R')$_5$, —$CH_2$—C(R')$_3$, —$C_3$(R')$_7$, —$C_2H_4$—C(R')$_3$, —$C_2H_4$—CH=$CH_2$, —CH=CH—$C_2H_5$, —CH=C ($CH_3$)$_2$, —$CH_2$—CH=CH—$CH_3$, —CH=CH—CH=$CH_2$, —$C_2H_4$—C≡CH, —C≡C—$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH ($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C ($CH_3$)—CH=$CH_2$, —CH=CH—C($CH_3$)=$CH_2$, —$CH_2$—CH=C($CH_3$)$_2$, C($CH_3$)=C($CH_3$)$_2$, —$C_3H_6$—C≡CH, —C≡C—$C_3H_7$, —$C_2H_4$—C≡C—$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$) =$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH ($CH_3$)—CH($CH_3$)—$C_2H_5$, —$CH_2$—CH($CH_3$)—CH($CH_3$)$_2$, —$CH_2$—C($CH_3$)$_2$—$C_2H_5$, —C($CH_3$)$_2$—$C_3H_7$, —C($CH_3$)$_2$—CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$;

R' is independently H, —$CO_2$R", —CONHR", —CR"O, —$SO_2$NR", —NR"—CO-haloalkyl, —$NO_2$, —NR"—$SO_2$-haloalkyl, —NR"—$SO_2$-alkyl, —$SO_2$-alkyl, —NR"—CO-alkyl, —CN, alkyl, cycloalkyl, aminoalkyl, alkylamino, alkoxy, —OH, —SH, alkylthio, hydroxyalkyl, hydroxyalkylamino, halogen, haloalkyl, haloalkyloxy, aryl, arylalkyl or heteroaryl;

R" is independently hydrogen, haloalkyl, hydroxyalkyl, alkyl, cycloalkyl, aryl, heteroaryl or aminoalkyl;

a cycloalkyl group denotes a non-aromatic ring system containing three to eight carbon atoms, preferably four to eight carbon atoms, wherein one or more of the carbon atoms in the ring can be substituted by a group X, X is N, $NR^6$, O, S, SO $SO_2$; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group;

an alkylthio group denotes an S-alkyl group, the alkyl group being as defined above.

a haloalkyl group denotes an alkyl group which is substituted by one to five halogen atoms, the alkyl group being as defined above; the haloalkyl group is preferably a —C($R^{10}$)$_3$, —$CR^{10}$($R^{10'}$)$_2$, —$CR^{10}$($R^{10'}$)$R^{10''}$, —$C_2$($R^{10}$)$_5$, —$CH_2$—C($R^{10}$)$_3$, —$CH_2$—$CR^{10}$($R^{10'}$)$_2$, —$CH_2$—$CR^{10}$ ($R^{10'}$)$R^{10''}$, —$C_3$($R^{10}$)$_7$ or —$C_2H_4$—C($R^{10'}$)$_3$, wherein $R^{10}$, $R^{10'}$, $R^{10''}$ represent F, Cl, Br or I, preferably F;

a hydroxyalkyl group denotes an HO-alkyl group, the alkyl group being as defined above;

a haloalkyloxy group denotes an alkoxy group which is substituted by one to five halogen atoms, the alkyl group being as defined above; the haloalkyloxy group is preferably a —OC($R^{10}$)$_3$, —$OCR^{10}$($R^{10'}$)$_2$, —$OCR^{10}$($R^{10'}$)$R^{10''}$, —$OC_2$($R^{10}$)$_5$, —$OCH_2$—C($R^{10}$)$_3$, —$OCH_2$—$CR^{10}$($R^{10'}$)$_2$, —$OCH_2$—$CR^{10}$($R^{10'}$)$R^{10''}$, —$OC_3$($R^{10}$)$_7$ or —$OC_2H_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$-N— group or HO-alkyl-NH— group, the alkyl group being as defined above;

an alkylamino group denotes an HN-alkyl or N-dialkyl group, the alkyl group being as defined above;

a halogen group is chlorine, bromine, fluorine or iodine, fluorine being preferred;

an aryl group denotes an aromatic group having five to fifteen carbon atoms, which can optionally be substituted by one or more substituents R', where R' is as defined above; the aryl group is preferably a phenyl group, -o-$C_6H_4$—R', -m-$C_6H_4$—R', -p-$C_6H_4$—R';

an arylalkyl group denotes an alkyl group substituted by an aryl group, the alkyl and the aryl group being as defined above; the arylalkyl group is preferably —$CH_2$Ph, —$C_2H_4$Ph, —CH=CH-Ph, —C≡C-Ph, -o-$CH_2$—$C_6H_4$—R', -m-$CH_2$—$C_6H_4$—R', -p-$CH_2$—$C_6H_4$—R';

a haloaryl group denotes an aryl group which is substituted by one to five halogen atoms, the aryl group being as defined above; the haloaryl group is preferably a —$C_6H_2$($R^{10}$)$_3$, —$C_6H_2R^{10}$($R^{10'}$)$_2$, —$C_6H_2R^{10}$($R^{10'}$)$R^{10''}$, —$C_6$($R^{10}$)$_5$, wherein $R^{10}$, $R^{10'}$, $R^{10''}$ represent F, Cl, Br or I, preferably F;

a haloalkylaryl group denotes an arylalkyl group which is substituted by one to five halogen atoms, the arylalkyl group being as defined above; the haloalkylaryl group is preferably a —CH$_2$—C$_6$H$_2$R$^{10}$(R$^{10'}$)$_2$, —CH$_2$—C$_6$H$_2$R$^{10}$(R$^{10'}$) R$^{10''}$, or —C$_2$H$_4$—C$_6$H$_2$(R$^{10}$)$_3$, wherein R$^{10}$, R$^{10'}$, R$^{10''}$ represent F, Cl, Br or I, preferably F;

a heteroaryl group denotes a 5- or 6-membered heterocyclic group which contains at least one heteroatom like O, N, S. This heterocyclic group can be fused to another ring. For example, this group can be selected from a thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, 1H-tetrazol-2-yl, 1H-tetrazol-3-yl, tetrazolyl, indolyl, indolinyl, benzo-[b]-furanyl, benzo[b]thiophenyl, benzimidazolyl, benzothiazolyl, quinazolinyl, quinoxazolinyl, or preferably quinolinyl, tetrahydroquinolinyl, isoquinolinyl, tetrahydroisoquinolinyl group. This heterocyclic group can optionally be substituted by one or more substituents R', where R' is as defined above.

In a preferred embodiment, the present invention is directed to a compound as defined above, wherein p=1 and n=0.

In another preferred embodiment, the present invention is directed to a compound as defined above, wherein p=1, n=0, R$^5$ independently represents alkyl, cycloalkyl, aminoalkyl, alkoxy, —OH, —SH, alkylthio, hydroxyalkyl, haloalkyl, haloalkyloxy, aryl, arylalkyl, haloaryl, haloalkylaryl, heteroaryl or R$^5$ and R$^6$ form a ring together with N-atom to which they are attached.

In another preferred embodiment, the present invention is directed to a compound as defined above, wherein p=1, n=0, R$^6$ independently represents alkyl, cycloalkyl, aminoalkyl, alkoxy, —OH, —SH, alkylthio, hydroxyalkyl, haloalkyl, haloalkyloxy, aryl, heteroaryl or R$^6$ is absent in case it forms a ring with R$^5$.

In another preferred embodiment, the present invention is directed to a compound as defined above, wherein p=0 and n=0.

In another preferred embodiment, the present invention is directed to a compound as defined above, wherein p=0, n=0, and R$^4$ independently represents alkyl, cycloalkyl, aminoalkyl, alkoxy, —OH, —SH, alkylthio, hydroxyalkyl, haloalkyl, haloalkoxy, aryl heteroaryl or

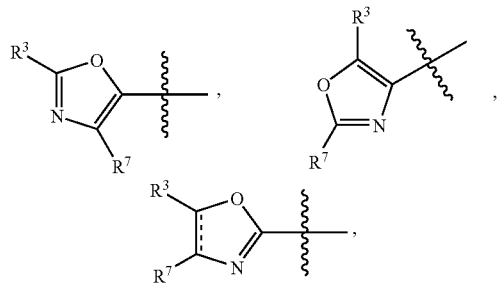

wherein the bond between CR$^3$ and CR$^7$ is a single or double bond.

In another preferred embodiment, the present invention is directed to a compound as defined above, wherein p=0 and n=1.

In another preferred embodiment, the present invention is directed to a compound as defined above, wherein p=0, n=1, and m=0.

In another preferred embodiment, the present invention is directed to a compound as defined above, wherein p=0, n=1, and m=1.

In another preferred embodiment, the present invention is directed to a compound as defined above, wherein p=1 and n=1.

In another preferred embodiment, the present invention is directed to a compound as defined above, wherein p=1, n=1, and m=0.

In another preferred embodiment, the present invention is directed to a compound as defined above, wherein p=1, n=1, and m=1.

In another preferred embodiment, the present invention is directed to a compound as defined above, wherein p=1, n=1, m=1, and R$^1$ is

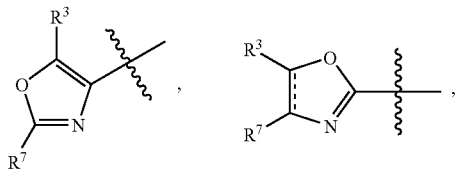

wherein the bond between CR$^3$ and CR$^7$ is a single or double bond.

In another preferred embodiment, the present invention is directed to a compound as defined above, wherein p=1, n=1, m=1, and R$^1$ is

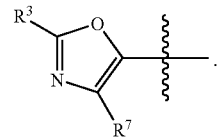

In another preferred embodiment, the present invention is directed to a compound as defined above, wherein p=1, n=1, m=1, R$^1$ is

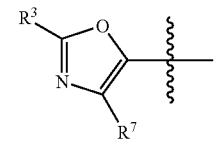

and R$^3$ is alkyl, cycloalkyl, aminoalkyl, alkoxy, —OH, —SH, alkylthio, hydroxyalkyl, haloalkyl, haloalkyloxy, aryl or heteroaryl.

In another preferred embodiment, the present invention is directed to a compound as defined above, wherein p=1, n=1, m=1, and R$^1$ is CN.

The invention also provides a pharmaceutical composition comprising a compound of formula (I) in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered. Examples of physiologically functional derivatives are prodrugs such as those described below in the present application.

In another aspect, the present invention also provides a method for the treatment or prophylaxis of a condition where there is an advantage in inhibiting T-cell proliferation or treatment of viral infections which comprises the administration of an effective amount of a compound of formula (I) and physiologically acceptable salts or physiologically functional derivatives thereof.

The invention is also directed to the use of compounds of the formula (I) of their pharmacologically tolerable salts or physiologically functional derivatives for the production of a medicament for the prevention and treatment of lyphoproliferative diseases, or diseases where inhibition of the guanosin biosynthesis or inhibition of Kv1.3 ion channels or inhibition of IMPDH is of benefit.

In particular, the present invention is directed to a method for the treatment of a disease or a therapeutic indication in which inhibition of cell proliferation is beneficial comprising administering to a mammal an effective amount of a novel compound as defined in the claims or a physiologically functional derivative or a pharmacologically tolerable salt thereof.

Furthermore, the present invention relates to a method for the treatment of viral disease comprising administering to a mammal an effective amount of a novel compound as defined in the claims or a physiologically functional derivative or a pharmacologically tolerable salt thereof.

Furthermore, the present invention relates to a method for the treatment of a disease or a therapeutic indication selected from the group consisting of rheumatism, acute immunological disorders, autoimmune diseases, diseases caused by malignant cell proliferation, inflammatory diseases, diseases that are caused by protozoal infestations in humans and animals, diseases that are caused by viral infections and Pneumocystis carinii, fibrosis, uveitis, rhinitis, asthma and athropathy comprising administering to a mammal an effective amount of a novel compound as defined in the claims or a physiologically functional derivative or a pharmacologically tolerable salt thereof.

The present invention furthermore relates to the use of a novel compound as defined in the claims for the inhibition of T-cell proliferation or treatment of viral infections.

In addition, the present invention provides methods for preparing the compounds of the invention such as compounds of formula (I).

The compounds of formula (I) may be obtained via various methods.

The syntheses of some intermediates can be achieved by methods described in WO02/070467A1. Other intermediates can be obtained my methods as described by Murali Dhar T G, et. al. *Bioorg Med Chem Lett*, 12, 3305-3308, 2002; Murali Dhar T G, et. al. *J Med Chem*, 45, 2127-2130, 2002; Gu H H, et. al. *Bioorg Med Chem Lett*, 12, 1323-1326, 2002; Watterson S H, et. al. *Bioorg Med Chem Lett*, 13, 543-546, 2003; Iwanowitz E J, et. al. *Bioorg Med Chem Lett*, 13, 2059-2063, 2003; Murali Dhar T G, et. al. *Bioorg Med Chem Lett*, 13, 3557-3560, 2003. Other intermediates, especially the oxazolines, can be made by methods described in: Katrizky A R et al. *JOC* 69, 3, 811-814, 2004 and references within.

In preferred embodiments of the methods of the invention the following methods of synthesis are used.

Method 1. Synthesis of 4-sulfonylamidobenzyl-phenylurea

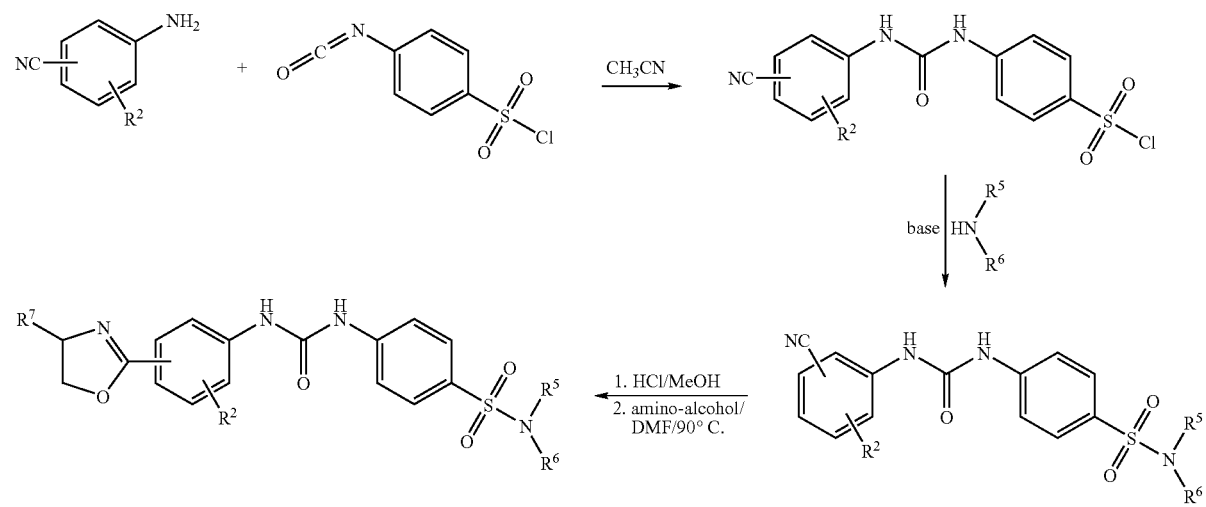

Method 2. Synthesis of 3-sulfonylamidobenzyl-phenylurea

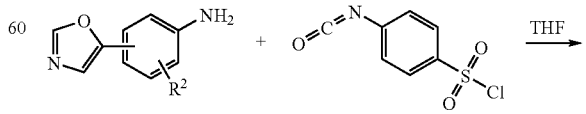

-continued

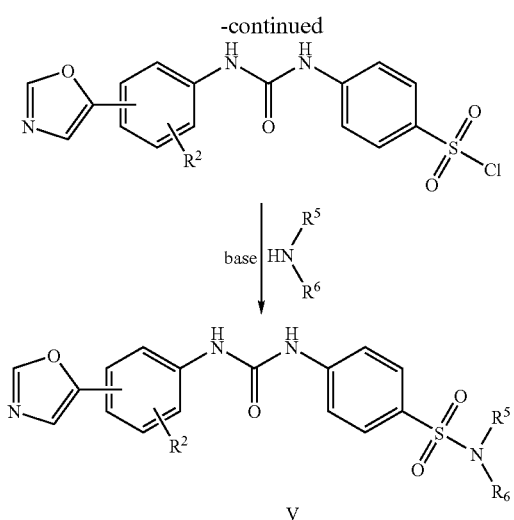

In a preferred embodiment, in the compounds of formula (I), $R^2$ is hydrogen or an alkoxy group, like methoxy or ethoxy.

In another preferred embodiment, in the compounds of formula (I), $R^3$ is hydrogen, phenyl, or benzyl.

In another preferred embodiment, in the compounds of formula (I), $R^7$ is hydrogen, phenyl, or benzyl.

In another preferred embodiment, in the compounds of formula (I),

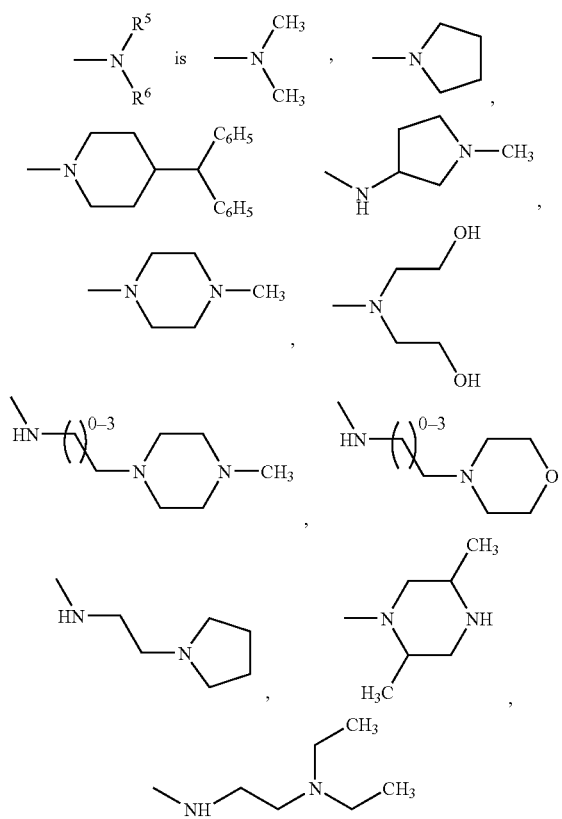

In another preferred embodiment, in the compounds of formula (I), Y is CO.

In formula (I) m is preferably 1.
In formula (I) p is preferably 1.

The compounds of the formula (I), to be used according to the invention can form salts with inorganic or organic acids or bases. Examples of such salts are, for example, alkali metal salts, in particular sodium and potassium salts, or ammonium salts where adequate.

The compounds of the present invention can be used for a variety of human and animal diseases, preferably human diseases, where inhibition of the pyrimidine metabolism is beneficial. Such diseases are:

fibrosis, uveitis, rhinitis, asthma or arthropathy, in particular, arthrosis all forms of rheumatism acute immunological events and disorders such as sepsis, septic shock, endotoxic shock, Gram-negative sepsis, toxic shock syndrome, acute respiratory distress syndrome, stroke, reperfusion injury, CNS injury, serious forms of allergy, graft versus host and host versus graft reactions, Alzheimer's or pyresis, restenosis, chronic pulmonary inflammatory disease, silicosis, pulmonary sarcosis, bone resorption disease. These immunological events also include a desired modulation and suppression of the immune system;

all types of autoimmune diseases, in particular rheumatoid arthritis, rheumatoid spondylitis, osteoarthritis, gouty arthritis, multiple sclerosis, insulin dependent diabetes mellitus and non-insulin dependent diabetes, and lupus erythematoidis, ulcerative colitis, Morbus Crohn, inflammatory bowel disease, as well as other chronic inflammations, chronic diarrhea;

dermatological disorders such as psoriasis progressive retinal atrophy all kinds of infections including opportunistic infections.

The compounds according to the invention and medicaments prepared therewith are generally useful for the treatment of cell proliferation disorders, for the treatment or prophylaxis, immunological diseases and conditions (as for instance inflammatory diseases, neuroimmunological diseases, autoimmune diseases or other).

The compounds of the present invention are also useful for the development of immunomodulatory and anti-inflammatory medicaments or, more generally, for the treatment of diseases where the inhibition of the T-cell proliferation is beneficial.

The compounds of the present invention are also useful for the treatment of diseases which are caused by malignant cell proliferation, such as all forms of hematological and solid cancer. Therefore the compounds according to the invention and medicaments prepared therewith are generally useful for regulating cell activation, cell proliferation, cell survival, cell differentiation, cell cycle, cell maturation and cell death or to induce systemic changes in metabolism such as changes in sugar, lipid or protein metabolism. They can also be used to support cell generation poiesis, including blood cell growth and generation (prohematopoietic effect) after depletion or destruction of cells, as caused by, for example, toxic agents, radiation, immunotherapy, growth defects, malnutrition, malabsorption, immune dysregulation, anemia and the like or to provide a therapeutic control of tissue generation and degradation, and therapeutic modification of cell and tissue maintenance and blood cell homeostasis.

These diseases and conditions include but are not limited to cancer as hematological (e.g. leukemia, lymphoma, myeloma) or solid tumors (for example breast, prostate, liver, bladder, lung, esophageal, stomach, colorectal, genitourinary, gastrointestinal, skin, pancreatic, brain, uterine, colon, head and neck, and ovarian, melanoma, astrocytoma, small cell lung cancer, glioma, basal and squameous cell carcinoma, sarcomas as Kaposi's sarcoma and osteosarcoma), treatment of disorders involving T-cells such as aplastic anemia and DiGeorge syndrome, Graves' disease.

The compounds of the present invention can be used to treat viral infections in general and viral infections such as Hepatitis C, Respiratory sycytia virus, Papiloma Virus, Hepatitis B, Herpes Virus Infections, HCMV specifically.

The compounds of formula (I), and their pharmacologically acceptable salts can be administered to animals, preferably to mammals, and in particular to humans, dogs and chickens as therapeutics per se, as mixtures with one another or in the form of pharmaceutical preparations which allow enteral or parenteral use and which as active constituent contain an effective dose of at least one compound of the formula (I) or a salt thereof, in addition to customary pharmaceutically innocuous excipients and additives. The compounds of formula (I), can also be administered in form of their salts, which are obtainable by reacting the respective compounds with physiologically acceptable acids and bases.

The therapeutics can be administered orally, e.g. in the form of pills, tablets, coated tablets, sugar coated tablets, hard and soft gelatin capsules, solutions, syrups, emulsions or suspensions or as aerosol mixtures. Administration, however, can also be carried out rectally, e.g. in the form of suppositories, or parenterally, e.g. in the form of injections or infusions, or percutaneously, e.g. in the form of ointments, creams or tinctures.

In addition to the active compounds of formula (I), the pharmaceutical composition can contain further customary, usually inert carrier materials or excipients. Thus, the pharmaceutical preparations can also contain additives, such as, for example, fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for changing the osmotic pressure, coating agents or antioxidants. They can also contain two or more compounds of the formula (I), or their pharmacologically acceptable salts and also other therapeutically active substances.

Thus, the compounds of the present invention can be used in the form of one substance alone or in combination with other active compounds—for example with medicaments already known for the treatment of the aforementioned diseases, whereby in the latter case a favorable additive, amplifying effect is noticed. Suitable amounts to be administered to humans range from 5 to 500 mg.

To prepare the pharmaceutical preparations, pharmaceutically inert inorganic or organic excipients can be used. To prepare pills, tablets, coated tablets and hard gelatin capsules, for example, lactose, corn starch or derivatives thereof, talc, stearic acid or its salts, etc. can be used. Excipients for soft gelatin capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight preferably 1 to 50 mg/kg. Suitable dosage rates for larger mammals, for example humans, are of the order of from about 10 mg to 3 g/day, conveniently administered once, in divided doses 2 to 4 times a day, or in sustained release form.

In general, a daily dose of approximately 10 mg to 5000 mg, preferably 50 to 500 mg, per human individual is appropriate in the case of the oral administration which is the preferred form of administration according to the invention. In the case of other administration forms too, the daily dose is in similar ranges.

The compounds of formula (I), can also be used in the form of a precursor (prodrug) or a suitably modified form, that releases the active compound in vivo.

EXAMPLES AND TECHNICAL PROCEDURES

Synthesis Method 1:

Aminobenzonitrile (or substituted aminobenzonitrile) (1 eq.) and chlorosulfonylphenylisocyanate (1 eq) were dissolved in anhydrous dichloromethane under inert atmosphere and stirred at ambient temperature for 18 h. The precipitate was filtered off and dried in vacuo or else the reaction mixture was concentrated to dryness in vacuo. The dry substance (1 eq) was added to a solution of the appropriate amine (1-2 eq.) and triethylamine (1-2 eq.) in anhydrous acetonitrile at 0° C. under inert atmosphere. The reaction mixture was warmed to ambient temperature for 10 min and stirred for a further 18 h. It was then concentrated in vacuo, water was added and the resulting precipitate was filtered and dried in the vacuo. The product is purified by flash chromatography using dichlormethan/methanol mixtures.

Method 1a.

Sulfonamide (or cyano-biphenyl-urea) (1 g) was suspended in methanolic hydrochloridic acid (100 ml) at 0° C. under inert atmosphere and stirred for 20 h during which the mixture warmed to rt. The solution was concentrated under reduced pressure and diethylether was added. The resulting precipitate was filtered off, washed with diethylether and dried in the vacuum. The compounds are used without further purifications.

Method 1b.

Iminoethers obtained in 1b were dissolved in dry DMF, diisopropylethylamine (1 eq.) and substituted 2-aminoethanol (1 eq.) was added. The mixture was heated to 40° C. for 6 hrs. The solvent was removed in the vacuum and the residue chromatographed by preparative HPLC to give the final compounds in yields between 60 to 80%.

EXAMPLES

NMR spectra: Bruker Avance 300 MHz. The spectra were recorded in $(CD_3)_2CO$ at 300 MHz ($^1$H NMR), respectively, using the residual solvent peak as an internal standard ($\delta$=2.05). Analytical LC/ESI-MS: 2× Waters 600 Multisolvent Delivery System. 50 µl sample loop. Column, Chromolith Speed ROD RP18e (Merck, Darmstadt), 50×4.6 mm, with 2 µm prefilter (Merck). Eluent A, $H_2O$+0.1% $HCO_2H$; eluent B, MeCN. Gradient, 5% B to 100% B within 5 min; flow 3 ml/min. Waters LCZ single quadrupol mass spec trometer with electrospray source. MS method, MS8minPM-80-800-20 V; positive/negative ion mode scanning, m/z 80-800 in 1 s; capillary, 3.5 kV; cone voltage, 20 V; multiplier voltage, 400 V; probe and desolvation gas temperature, 120° C. and 350° C., respectively. Waters 2487 Dual λ Absorbance Detector, set to 254 nm.

| Cpd. | Structure | NMR-Data | [M + H]$^+$ |
|---|---|---|---|
| 1 | 4-{3-[4-(4-(R)-Phenyl-4,5-dihydro-oxazol-2-yl)-phenyl]-ureido}-N-(3,4,5-trifluoro-benzyl)-benzenesulfonamide | $^1$H: δ=4.16-4.21(m, 3H, CH$_2$, CH), 4.82-4.88(m, 1H, CH$_2$), 5.38-5.44(m, 1H, CH$_2$), 5.38-5.44(m, 15H, CH$_{Ar}$). | 581.14 |
| 2 | 4-{3-[4-(4-(S)-Phenyl-4,5-dihydro-oxazol-2-yl)-phenyl]-ureido}-N-(3,4,5-trifluoro-benzyl)-benzenesulfonamide | $^1$H: δ=4.16-4.21(m, 3H, CH$_2$, CH), 4.82-4.88(m, 1H, CH$_2$), 5.38-5.44(m, 1H, CH$_2$), 5.38-5.44(m, 15H, CH$_{Ar}$). | 581.14 |
| 3 | 4-{3-[4-(4-(R)-Benzyl-4,5-dihydro-oxazol-2-yl)-phenyl]-ureido}-N-(3,4,5-trifluoro-benzyl)-benzenesulfonamide | $^1$H: δ=2.77-3.1(m, 2H, CH$_2$), 4.08-4.18(m, 3H, CH$_2$, CH), 4.36-4.42(m, 1H, CH$_2$), 4.50-4.60(m, H, 1CH$_2$), 6.99-7.87(m, 15H, CH$_{Ar}$). | 595.15 |
| 4 | 4-{3-[4-(4-(S)-Benzyl-4,5-dihydro-oxazol-2-yl)-phenyl]-ureido}-N-(3,4,5-trifluoro-benzyl)-benzenesulfonamide | $^1$H: δ=2.77-3.1(m, 2H, CH$_2$), 4.08-4.18(m, 3H, CH$_2$, CH), 4.36-4.42(m, 1H, CH$_2$), 4.50-4.60(m, 1H, CH$_2$), 6.99-7.87(m, 15H, CH$_{Ar}$). | 595.15 |
| 5 | 1-[3-(4-(R)-Phenyl-4,5-dihydro-oxazol-2-yl)-phenyl]-3-(3-trifluoromethyl-phenyl)-urea | $^1$H: δ=4.22(m$_c$, 1H, 1CH$_2$), 4.84-4.91(m, 1H, CH$_2$), 5.40-5.47(m, 1H CH$_2$), 7.25-8.27(m, 13H, CH$_{Ar}$). | 426.14 |
| 6 | 1-[3-(4-(S)-Phenyl-4,5-dihydro-oxazol-2-yl)-phenyl]-3-(3-trifluoromethyl-phenyl)-urea | $^1$H: δ=4.22(m$_c$, 1H, CH$_2$), 4.84-4.91(m, 1H, CH$_2$), 5.40-5.47(m, 1H CH$_2$), 7.25-8.27(m, 13H, CH$_{Ar}$). | 426.14 |
| 7 | 1-[3-(4-(R)-Benzyl-4,5-dihydro-oxazol-2-yl)-phenyl]-3-(3-trifluoromethyl-phenyl)-urea | $^1$H: δ=2.80-3.11(m, 2H, CH$_2$), 4.13(m$_c$, 1H, CH$_2$), 4.39-4.45(m, 1H, CH$_2$), 4.53-4.63(m, 1H CH$_2$), 7.18-8.16(m, 13H, CH$_{Ar}$). | 440.15 |
| 8 | 1-[3-(4-(S)-Benzyl-4,5-dihydro-oxazol-2-yl)-phenyl]-3-(3-trifluoromethyl-phenyl)-urea | $^1$H: δ=2.80-3.11(m, 2H, CH$_2$), 4.13(m$_c$, 1H, CH$_2$), 4.39-4.45(m, 1H, CH$_2$), 4.53-4.63(m, 1H CH$_2$), 7.18-8.16(m, 13H, CH$_{Ar}$). | 440.15 |
| 9 | 4-[4-(4-(R)-Phenyl-4,5-dihydro-oxazol-2-yl)-benzenesulfonyl]-morpholine | | 373.11 |
| 10 | N,N-Bis-(2-hydroxy-ethyl)-4-(4-(R)-phenyl-4,5-dihydro-oxazol-2-yl)-benzenesulfonamide | | 391.12 |
| 11 | 4-[4-(4-(R)-Benzyl-4,5-dihydro-oxazol-2-yl)-benzenesulfonyl]-morpholine | | 387.13 |
| 12 | 4-(4-(R)-Benzyl-4,5-dihydro-oxazol-2-yl)-N,N-bis-(2-hydroxy-ethyl)-benzenesulfonamide | | 405.14 |
| 13 | 4-[4-(4-(S)-Benzyl-4,5-dihydro-oxazol-2-yl)-benzenesulfonyl]-morpholine | | 387.13 |
| 14 | 4-(4-(S)-Benzyl-4,5-dihydro-oxazol-2-yl)-N,N-bis-(2-hydroxy-ethyl)-benzenesulfonamide | | 405.14 |
| 15 | 1-(4-Cyano-3-methoxy-phenyl)-3-[4-(morpholine-4-sulfonyl)-phenyl]-urea | $^1$H: δ=2.94(m$_c$, 4H, CH$_2$); 3.68(m$_c$, 4H, CH$_2$); 3.94(s, 3H, CH$_3$); 7.1-7.9(m, 7H, CH$_{Ar}$); 8.78(s, 2H, NH). | 417.12 |
| 16 | 1-[4-(Morpholine-4-sulfonyl)-phenyl]-3-[4-(4-(R)-phenyl-4,5-dihydro-oxazol-2-yl)-phenyl]-urea | $^1$H: δ=2.94(m$_c$, 4H, CH$_2$), 3.68(m$_c$, 4H, CH$_2$), 4.19(m$_c$, 1H, CH), 4.82-4.88(m, 1H, CH$_2$), 5.38-5.44(m, 1H, CH$_2$), 7.25-7.99(m, 13H CH$_{Ar}$). | 507.16 |
| 17 | 1-[4-(Morpholine-4-sulfonyl)-phenyl]-3-[4-(4-(S)-phenyl-4,5-dihydro-oxazol-2-yl)-phenyl]-urea | $^1$H: δ=2.94(m$_c$, 4H, CH$_2$), 3.68(m$_c$, 4H, CH$_2$), 4.19(m$_c$, 1H, CH), 4.82-4.88(m, 1H, CH$_2$), 5.38-5.44(m, 1H, CH$_2$), 7.25-7.99(m, 13H CH$_{Ar}$). | 507.16 |
| 18 | 1-[4-(4-(R)-Benzyl-4,5-dihydro-oxazol-2-yl)-phenyl]-3-[4-(morpholine-4-sulfonyl)-phenyl]-urea | $^1$H: δ=2.78-2.85(m, 1H, CH$_2$), 2.94(m$_c$, 4H, CH$_2$), 3.03-3.09(m, 1H, CH$_2$), 3.08(m$_c$, 4H, CH$_2$), 4.05-4.13(m, 1H, CH$_2$), 4.37-4.42(m, 1H, CH$_2$), 4.55(m$_c$, 1H, CH), 7.17-7.89(m, 13H, CH$_{Ar}$). | 521.18 |
| 19 | 1-(4-Cyano-phenyl)-3-[4-(morpholine-4-sulfonyl)-phenyl]-urea | $^1$H: δ=2.94(m$_c$, 4H, CH$_2$), 3.68(m$_c$, 4H, CH$_2$), 7.66-7.83(m, 8H, CH$_{Ar}$), 9.25(s, 2H, NH). | 387.13 |

-continued

| Cpd. | Structure | NMR-Data | [M + H]+ |
|---|---|---|---|
| 20 | 1-[4-(4,5-Dihydro-oxazol-2-yl)-phenyl]-3-(4-trifluoromethyl-phenyl)-urea | $^1$H: δ=3.99($m_c$, 2H, 1$CH_2$), 4.42($m_c$, 2H, 1$CH_2$), 7.30-8.18(m, 8H, $CH_{Ar}$), 8.32(s, 1H, NH), 8.44(s, 1H, NH). | 350.10 |
| 21 | N-Naphthalen-1-ylmethyl-4-{3-[4-(4-(R)-phenyl-4,5-dihydro-oxazol-2-yl)-phenyl]-ureido}-benzenesulfonamide | | 577.18 |
| 22 | 4-{3-[3-(4-(S)-Benzyl-4,5-dihydro-oxazol-2-yl)-phenyl]-ureido}-N-(3,4,5-trifluoro-benzyl)-benzenesulfonamide | | 595.15 |

Biological Methods and Results:

T Lyphocyte Proliferation Assay:

Inhibition of stimulated peripheral blood monocyte (PBMC) stimulation

PBMCs were isolated from the blood of healthy volunteers with the help of ACCUSPIN™ System Histopaque®-1077 tubes, washed and resuspended with $10^6$ cells/ml in Dulbecco's modified eagles medium, containing 10% fetal calf serum and 2 mM Glutamine.

The cells were stimulated with 2 µg/ml phytohemoagglutinin in the presence of test compound or blank vehicle for 72 h. 4 h prior to the end of the incubation period, 5-bromo-2'-desoxyuridine (BrdU) was added to label the proliferating cells. After the incubation, the cells were separated by centrifugation and the culture supernatant removed. Incorporated BrdU was quantified with the help of an enzyme-linked immunosorbent assay.

For the determination of the $IC_{50}$ values (concentration of inhibitor required for 50% inhibition) at least four different inhibitor concentrations were applied. Each data point was recorded in triplicates. Curves were fitted with the a suitable program.

Example 1 and 22 showed $IC_{50}$ values <5 µM

Kv1.3-Assay:

Stable transfected L929 cells with Kv1.3 channels were grown in DMEM (Glutamax-I) media with 10% FCS, geneticin 330 µg/ml under 10% $CO_2$ atmosphere.

Whole-cell patch-clamp configuration, with an external bath solution of 160 mM NaCl, 4, 5 mM KCl, 1 mM $MgCl_2$, 2 mM $CaCl_2$, 5 mM HEPES, 10 mM EGTA and NaOH adjusted to pH 7.4. Internal pipette solution for recording was 155 mM KF, 2 mM $MgCl_2$, 10 mM HEPES, 10 mM EGTA with KOH adjusted to pH 7.2. Currents were activated by a 200-ms voltage step from a holding potential of −80 to 40 mV every 30 s. Holding potential −80 mV.

Each compound was tested on two different cells. The cell was perfused with external bath solution (black line), then the compound was applied (c=20 µM). The resulting stedy-state current traces are shown as red lines. Example 3, 5, 6, 7, 8 are blockers.

IMPDH Enzyme-Assay:

For measuring IMPDH activity in vitro, the substrate inosine monophosphate (IMP) and enzyme, with or without inhibitor, are mixed together. The reaction is initiated with the addition of the oxidized form of the cofactor nicotine amide adenine dinucleotide (NAD). The released NADH is measured at 340 nm.

The assay is performed in PMMA half micro liter cuvettes, the total assay volume is 1 mL. 500 µl of 2× assay buffer (200 mM Tris/HCl, pH 8.0, 200 mM KCl, 6 mM EDTA and 4 mM DTT) are mixed with 10 µL of a freshly prepared 20 mM IMP solution (0.2 mM final concentration) and 10 µL of enzyme (0.03 U/mL). An appropriate amount of inhibitor is dissolved in 100% DMSO. 10 µL of this solution are added to the assay mix (1% DMSO final concentration). Finally 455 µL of deionized water are added to give the final volume of 1 mL. The mixture is incubated for 10 min at 37° C. The enzyme reaction is started by addition of 25 µL of a 16 mM NAD solution (0.4 mM final concentration). Reaction is followed for 30 min at 37° C. at 340 nm. The enzyme reaction runs linear with respect to time during the 30 min. The slopes of the resulting curves are calculated and results are presented in % of residual activity, which is calculated as % activity=(slope with inhibitor/slope without inhibitor) *100.

For the determination of the $IC_{50}$ values (concentration of inhibitor required for 50% inhibition) at least four different inhibitor concentrations were applied. Each data point was recorded in triplicates. Curves were fitted with the a suitable program.

Example 15 showed an $IC_{50}$ value <5 µM.

Proteasome Assay:

The chymotryptic activity of the 20S proteasome (Immatics, Tubingen) was determined using a Tecan Ultra plate reader and Suc-LLVT-AMC as substrate (Bachem). In the wells of a black 96 well polypropylene plate, 2 µl of the respective inhibitor dissolved in DMSO were mixed with 50 µl substrate solution (25 mM HEPES pH 7.5 at 20° C., 0.5 mM EDTA and Suc-LLVT-AMC (in the appropriate concentration) and the reaction was initiated by adding 150 µl proteasome solution (1.3 µg/ml 20S proteasome in 25 mM HEPES pH 7.5 at 20° C., 0.5 mM EDTA, 0.033% (w/v) SDS). Substrate hydrolysis was followed by fluorescence spectroscopy (excitation wavelength: 360 nm; emission wavelength: 465 nm) for 20 min at 30° C. and initial velocities were calculated and expressed as change in relative fluorescence units (RFU) per second.

For the determination of the $IC_{50}$ values (concentration of inhibitor required for 50% inhibition) at least four different inhibitor concentrations were applied. Each data point was recorded in triplicates. Curves were fitted with the a suitable program.

Example $_1$ showed an $IC_{50}$ value <5 µM.

What is claimed is:

1. A compound of formula (I) and/or a salt thereof,

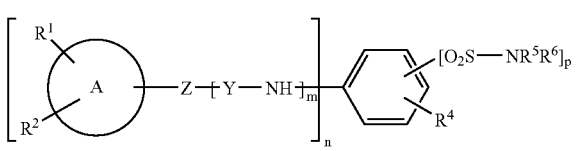

I wherein
Z is NH;
Y is C=O or C=S;
A is phenyl;
R¹ is —CN,

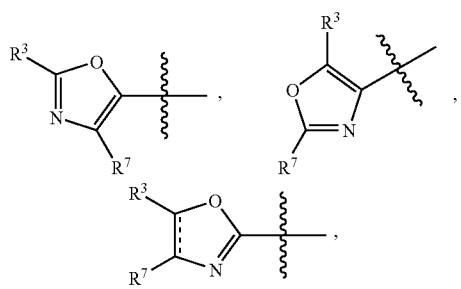

wherein the bond between CR³ and CR⁷ is a single or double bond;
R³ independently represents H, alkyl, cycloalkyl, aminoalkyl, alkoxy, —OH, —SH, alkylthio, hydroxyalkyl, haloalkyl, haloalkyloxy, aryl or heteroaryl;
R⁷ independently represents H, alkyl, cycloalkyl, aminoalkyl, alkoxy, —OH, —SH, alkylthio, hydroxyalkyl, haloalkyl, haloalkyloxy, aryl, arylalkyl or heteroaryl;
R² is H, an alkoxy, alkylthio, or haloalkyloxy, group;
R⁴ independently represents H, alkyl, cycloalkyl, aminoalkyl, alkoxy, —OH, —SH, alkylthio, hydroxyalkyl, haloalkyl, haloalkyloxy, aryl, heteroaryl or

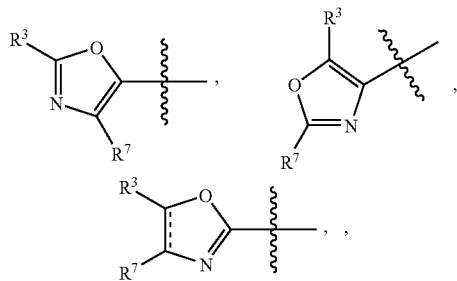

wherein the bond between CR³ and CR⁷ is a single or double bond;
R⁵ and R⁶ form a ring together with the N-atom to which they are attached;
m is 1;
n is 1; and
p is 1.

2. The compound according to claim 1, wherein p=1, n=1, m=1, and R¹ is

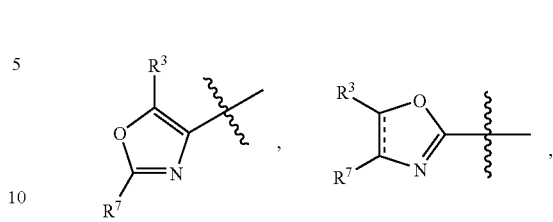

wherein the bond between CR³ and CR⁷ is a single or double bond.

3. The compound according to claim 1, wherein p=1, n=1, m=1, and R¹ is

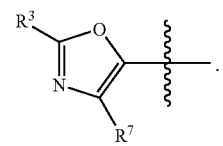

4. The compound according to claim 1, wherein p=1, n=1, m=1, R¹ is

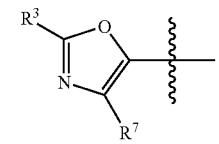

and R³ is alkyl, cycloalkyl, aminoalkyl, alkoxy, —OH, —SH, alkylthio, hydroxyalkyl, haloalkyl, haloalkyloxy, aryl or heteroaryl.

5. The compound according to claim 1, wherein p=1, n=1, m=1, and R¹ is CN.

6. A pharmaceutical composition comprising (1) a compound as defined in claim 1 in free form or in the form of a pharmaceutically acceptable salt; and (2) a pharmaceutically acceptable diluent or carrier.

7. A medicament comprising a compound according to claim 1 and a pharmaceutically acceptable excipient thereof.

8. A compound of formula (II) and/or a salt thereof

II

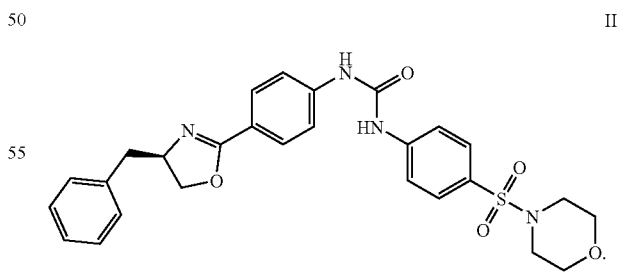

* * * * *